United States Patent [19]

Toda et al.

[11] Patent Number: 5,208,159
[45] Date of Patent: May 4, 1993

[54] ANTIBACTERIAL, ANTI-NEMATODE AND/OR PLANT-CELL ACTIVATING COMPOSITION, AND CHITINOLYTIC MICROORGANISMS FOR PRODUCING THE SAME

[75] Inventors: Takashi Toda, Shiga; Hideyuki Matsuda, Matsue, both of Japan

[73] Assignee: Toda Biosystem Laboratory, Japan

[21] Appl. No.: 523,388

[22] Filed: May 15, 1990

[30] Foreign Application Priority Data

May 16, 1989 [JP] Japan .................... 1-121989

[51] Int. Cl.$^5$ .................... C12N 1/20; A01N 63/00
[52] U.S. Cl. .................... 435/252.1; 424/93 D; 424/93 R; 435/252.4
[58] Field of Search .................... 424/93, 93 R, 93 C, 424/93 D; 435/252.1, 252.32, 253.6, 824, 843, 252.4

[56] References Cited

U.S. PATENT DOCUMENTS 3,857,935 12/1974 Chang .................... 424/93
4,751,081 6/1988 Suslow et al. .................... 424/93

FOREIGN PATENT DOCUMENTS 0171381 2/1986 European Pat. Off. .
0015878 6/1975 Japan .................... 435/171

OTHER PUBLICATIONS

Chemical Abstracts, vol. 85, No. 13, Sep. 27, 1976, p. 281.
Purification and Mode of Action of a Chitosanase from Penicillium islandicum, Dennis M. Fenton, et al., Journal of General Microbiology, 1981, pp. 151–165.

Primary Examiner—Douglas W. Robinson
Assistant Examiner—Susan M. Weber
Attorney, Agent, or Firm—Parkhurst, Wendel & Rossi

[57] ABSTRACT

Two strains of chitinolytic bacteria respectively named "Corynebacterium Bine-A" "Achromobacter Bine-B", which were deposited under deposit numbers FERM BP-2879 and FERM BP-2880 in the Fermentation Research Institute, Agency of Industrial Science and Technology, Japan. At least one of these strains is incubated on a chitin or chitosan medium, to prepare a culture material, which is usable directly as a solid antibacterial composition or fermented or aged to produce a solid antibacterial composition. Alternatively, water is added to the prepared culture material, and either of the liquid and solid phases may be used as an antibacterial, anti-nematode, and/or plant-cell activating composition.

4 Claims, 1 Drawing Sheet

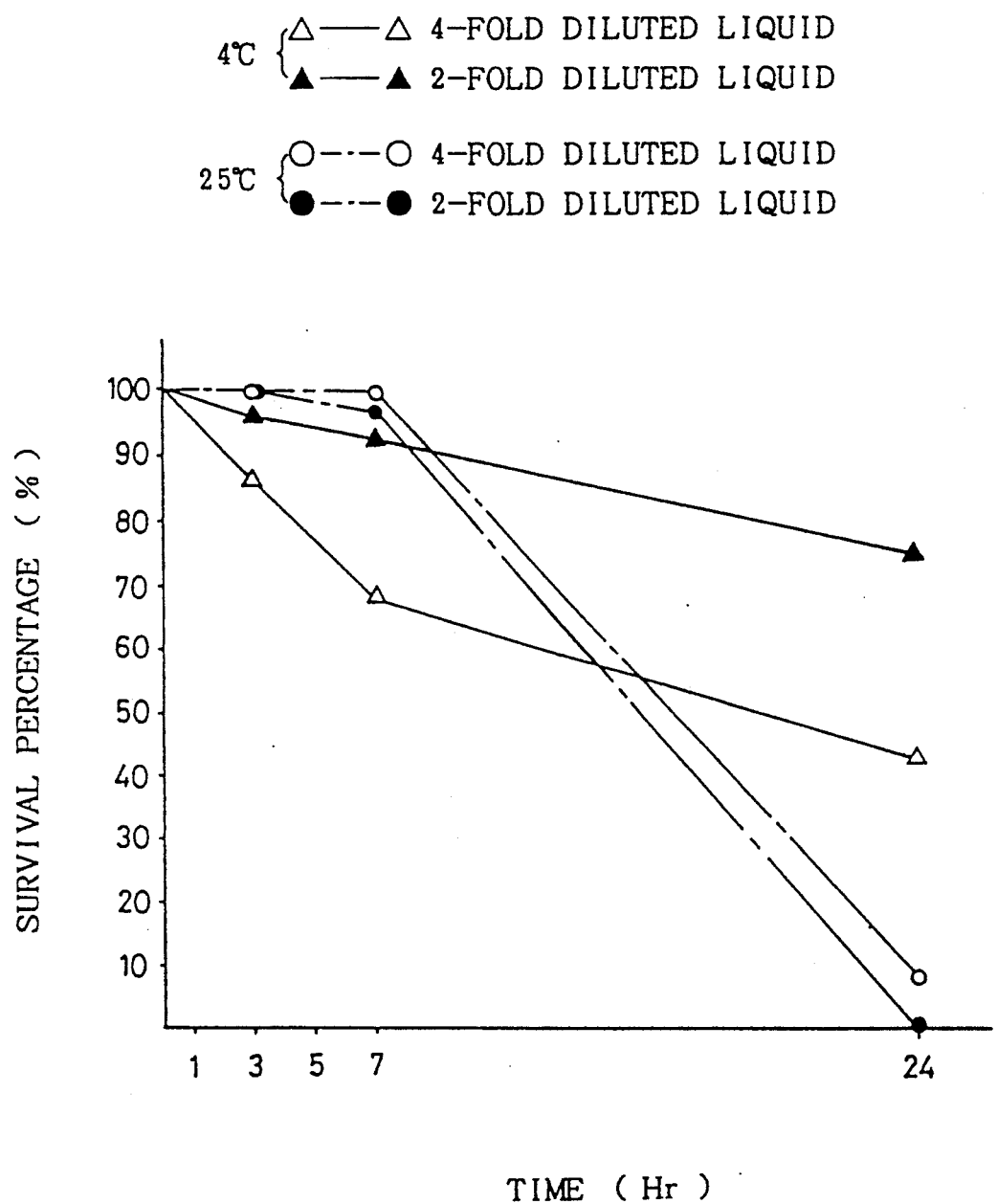

ANTIBACTERIAL, ANTI-NEMATODE AND/OR PLANT-CELL ACTIVATING COMPOSITION, AND CHITINOLYTIC MICROORGANISMS FOR PRODUCING THE SAME

BACKGROUND OF THE INVENTION

1. Field of the Invention

The present invention relates in general to a solid or liquid pharmaceutic material or composition having antimicrobial or antibacterial, anti-nematode and/or plant-cell activating activities, and strains of chitinolytic microorganisms or bacteria for producing such a pharmaceutic composition. More particularly, this invention is concerned with an antibacterial, anti-nematode and/or plant-cell activating composition consisting of a highly acidic culture liquid or a solid culture material, which is obtained by solid-liquid separation of a culture material which is prepared by incubating or cultivating a strain or strains of chitinolytic microorganisms or bacteria on a culture medium containing chitin or chitosan and to which water is added before the liquid or solid separation.

2. Discussion of the Prior Art

Various methods have been proposed for decomposing chitin or chitosan by using chitinolytic bacteria or microorganisms. These methods find applications in processing the integument of insects and crustaceans. Studies in this field have been accelerated by a recent recognition that cultures obtained by such chitinolytic microorganisms incubated on chitin or chitosan, and products produced during the cultivation of the microorganisms have useful pharmacological or pharmaceutic activities.

Having the above recognition, the inventors named in this application made an extensive research in an effort to find in nature the microorganisms which have high ability of decomposing chitin or chitosan and high ability of producing enzymes which decompose or lyse chitin or chitosan. The research resulted in finding strains of chitinolytic bacteria which exhibit a unique behavior depending upon pH of a culture medium. The inventors discovered that a culture liquid obtained from a culture material prepared by incubating such strains of bacteria (mircoorganisms) on a chitin or chitosan medium has excellent antibacterial, anti-nematode, and/or plant cellactivating activities.

SUMMARY OF THE INVENTION

It is therefore an object of the present invention to provide a pharmaceutic composition which is obtained from a culture material prepared by incubating chitinolytic bacteria and which has antibacterial, anti-nematode and/or plant-cell activating effects or activities.

A second object of the invention is to provide a bacterium which provides such a pharmaceutic composition.

The third object is to provide such a pharmaceutic composition whose antibacterial effect continues for a relatively long time.

The first object may be achieved according to one aspect of the present invention, which provides a composition consisting of a highly acidic culture liquid obtained in a process comprising: preparing a culture material by incubating on a culture medium containing chitin or chitosan, at least one of a strain of Corynebacterium Bine-A, a strain of Achromobacter Bine-B, and a mixture of microorganisms which includes at least one of said strains of Corynebacterium Bine-A and Achromobacter Bine-B; adding water to the prepared culture material, to obtain a mixture consisting of a liquid phase containing water-soluble components of the culture material, and a solid phase consisting of water-insoluble components of the culture material; and separating the liquid phase as the culture liquid from the solid phase. The strains named "Corynebacterium Bine-A" and "Achromobacter Bine-B" were deposited on May 1, 1989 in the Fermentation Research Institute, Agency of Industrial Science and Technology, Ministry of International Trade and Industry, located at 1-3, Higashi-1-chome, Tsukuba-shi, Ibaragi-ken, Japan, under deposit numbers FERM BP-2879 and FERM BP-2880, respectively.

The second object may be achieved according to another aspect of the invention, which provides a strain named "Corynebacterium Bine-A" deposited as indicated above, which is a chitinolytic bacterium capable of providing a composition as defined above.

The second object may also be achieved according to a further aspect of the invention, which provides a strain named "Achromobacter Bine-B" deposited as indicated above, which is a chitinolytic bacterium capable of providing a composition as defined above.

The third object may be attained according to a still further aspect of the invention, which provides an antibacterial composition consisting of a solid culture material prepared by incubating on a culture medium containing chitin or chitosan, at least one of the above-identified strains of chitinolytic bacteria (Corynebacterium Bine-A and Achromobacter Bine-B).

The third object may also be attained according to a yet further aspect of the invention which provides a solid antibacterial composition prepared in a process comprising the steps of: preparing a solid culture material by incubating on a culture medium containing chitin or chitosan, at least one of the above-identified strains of chitinolytic bacteria; mixing a phosphorus source substance and a nitrogen source substance with the solid culture material; and aging a mixture of the solid culture material and the phosphorus and nitrogen source substances.

The third object may also be attained according to another aspect of the invention, which provides a solid antibacterial composition prepared in a process comprising the steps of: preparing a solid culture material by incubating on a culture medium containing chitin or chitosan, at least one of the above-identified strains of chitinolytic bacteria; adding water to the solid culture material to prepare a water-containing culture; separating a solid phase of the water-containing culture by solid-liquid separation; mixing a phosphorus source substance, a nitrogen source substance and chitosan with the solid phase; and aging a mixture of the solid phase, the phosphorus and nitrogen source substances and the chitosan.

BRIEF DESCRIPTION OF THE DRAWING

In the accompanying drawing, the single figure is a graph showing an effect of an example of a culture liquid obtained by incubation of the microorganisms according to the present invention, when the culture liquid was used as an insecticide.

DETAILED DESCRIPTION OF THE INVENTION

A microorganism, which is one of the two species of the chitinolytic bacteria according to the present invention, was named "Corynebacterium Bine-A", while a microorganism which is the other species of the chitinolytic bacteria according to the invention was named "Achromobacter Bine-B". Strains of these chitinolytic bacteria were extracted from a water treatment effluent sludge produced by a food factory in Shiga prefecture, Japan for producing food (e.g., croquette) from potato. The sludge was mixed with rice chaff, and the mixture was fermented. Prior to the complete fermentation, chitosan was added to the sludge, and the strains of the bacteria were aerobically cultivated on chitosan. The culture of the bacteria was isolated as the Corynebacterium Bine-A and the Achromobacter Bine-B, the strains of which were deposited on May 1, 1989, in the Fermentation Research Institute, Agency of Industrial Science and Technology, Ministry of International Trade and Industry, located at 1-3, Higashi-1-chome, Tsukuba-shi, Ibaragi-ken, Japan, under deposit numbers FERM BP-2879 and FERM BP-2880, respectively. These chitinolytic bacteria have the following mycological characteristics and properties:

(I) Morphological Characteristics a) Corynebacterium Bine-A

This strain of bacteria belongs to the Gram-positive, short species (1.5~2.0μm×0.5~0.7μm) of Bacillus.

b) Achromobacter Bine-B

This strain of bacteria belongs to the Gram-negative species (1.5~2.0μm×0.5~0.7μm) of Bacillus, and has no spores.

(II) Culture Characteristics on Different Media a) Corynebacterium Bine-A (1) Broth agar Substantially no growth of the strain was observed.

(2) Colloidal chitin agar

A white colony having a slightly undulated periphery and substantially no convexity was observed. A narrow clear area appeared on the medium, around the periphery of the colony after two days of incubation at 30° C. More than ten days of incubation created a considerably large clear area around the periphery of the colony. The growth rate of the colony was lower than that of Achromobacter Bine-B.

Achromebacter Bine-B (1) Broth agar

A translucent, slight white colony irregularly spread over the medium. A growth of the colony was observed after one day of incubation at 30° C.

(2) Colloidal chitin agar

An initially transparent colony having a clear area vigorously grew as the incubation progressed. An area of the medium in which the bacteria grew well was transparent and appeared white. The clear area was almost equal to the colony area, more precisely, lightly larger than the colony area.

(III) Physiological Properties a) Corynebacterium Bine-A (1) Size of clear area on colloidal chitin agar medium (pH=7.0) at different temperatures

| Incubation (Day) | Temperature (°C.) | | | | |
|---|---|---|---|---|---|
| | 16 | 30 | 37 | 42 | 50 |
| 1 | — | — | — | — | — |
| 2 | — | 2-3 mm | 3 mm | 2 mm | — |
| 3 | — | 4-5 mm | 5-7 mm | 5-3 mm | — |
| 3 | — | (1-2 mm) | (2-3 mm) | (1-2 mm) | — |

—: No growth observed

The values in the parentheses represent the sizes of the colonies.

(2) Growth pH 1) (Luria Bertani) media (pH=7.8; 6.9; 5.9; 5.0; 4.0; 3.0; 1.9; and 1.0) A growth was observed on none of these media after 3 weeks of incubation.

2) Chitin media (pH=7.9; 7.2; 6.3; 5.5; 5.2; 3.9; 2.3 and 1.3) A growth density $OD_{660}$ representative of the number of the bacteria per unit area of each medium was optically measured with a radiation having a wavelength of 660nm. The measurements are indicated in the table below.

| Chitin Media pH | Days of Incubation | | | | | | |
|---|---|---|---|---|---|---|---|
| | 4 | 5 | 6 | 7 | 8 | 11 | 14 |
| 7.9 | 0.074 | 0.346 | 0.784 | 0.929 | 0.955 | | |
| 7.2 | 0.024 | 0.174 | 0.621 | 0.435 | 0.762 | | |
| 6.3 | — | — | — | 0.001 | 0.452 | 0.701 | |
| 5.5 | — | — | — | — | — | — | — |
| 5.2 | — | — | — | — | — | — | — |
| 3.9 | — | — | — | — | — | — | — |
| 2.3 | — | — | — | — | — | — | — |
| 1.3 | — | — | — | — | — | — | — |

3) A 1 ml volume of the culture liquid on each of the media (all the LB media having pH of 7.8-1.0, and the chitin media having pH of 5.5-1.3) on which no bacteria growth appeared in the tests 1) and 2) above, was transferred to a corresponding chitin medium having a pH value of 7.0. The culture liquids of the test 1) transferred to the pH 7.0 chitin medium were obtained after 3 weeks of incubation by a reciprocal shaker, while the culture liquids of the test 2) transferred to the pH 7.0 chitin medium were those obtained after 14 days of incubation. The growth density $OD_{660}$ of the bacteria on each pH 7.0 media after different days of incubation is indicated below.

| Original Culture (Medium) | (pH) | Days of Incubation | | | | |
|---|---|---|---|---|---|---|
| | | 4 | 5 | 6 | 7 | 30 |
| Chitin | 5.5 | 0.332 | 1.235 | 1.207 | | |
| | 5.2 | 0.388 | 1.177 | 1.409 | | |
| | 3.9 | 0.304 | 1.256 | 1.255 | | |
| | 2.3 | 0.200 | 0.914 | 1.370 | | |
| | 1.3 | — | — | — | — | — |
| LB | 7.8 | 0.632 | 1.160 | 1.382 | | |
| | 6.9 | 0.741 | 1.246 | 1.461 | | |
| | 5.9 | 0.452 | 0.770 | 1.248 | | |
| | 5.0 | 0.210 | 0.863 | 1.092 | | |
| | 4.0 | 0.225 | 0.901 | 0.896 | 1.351 | |
| | 3.0 | 0.256 | 0.684 | 0.626 | 1.249 | |
| | 1.9 | — | — | — | | |

-continued

| Original Culture (Medium) (pH) | Days of Incubation | | | | |
|---|---|---|---|---|---|
| | 4 | 5 | 6 | 7 | 30 |
| 1.0 | — | — | — | — | — |

It will be understood from the above results of the measurements on the pH 7.0 chitin media that the present strain of Corynebacterium Bine-A grows well at pH values around neutraility, and is dormant under relatively highly acidic conditions.

| | |
|---|---|
| (3) Nitrate reduction | Negative |
| (4) H$_2$S production | Negative |
| (5) Indole formation | Negative |
| (6) V-P test | Negative |
| (7) O-F test | Negative |
| (8) Methyl red test | Negative |
| (9) Catalase | Positive |
| (10) Oxidase | Negative |
| (11) Urease | Negative |
| (12) Acid and gas production from carbohydrates | Neither acid nor gas produced from: Glucose; Saccharose; Rhamnose; Sorbitol; Xylose; Lactose; Galactose; Maltose; Mannose; Arabinose; Fructose; and Mannitol |
| (13) Anaerobic cultivation | No growth | b) Achromobacter Bine-B (1) Diameter of clear area on colloidal chitin agar medium (pH=7.0) at different temperatures

| Incubation (Day) | Temperature (°C.) | | | | |
|---|---|---|---|---|---|
| | 16 | 30 | 37 | 42 | 50 |
| 1 | — | 2-3 mm | 2-3 mm | 2-3 mm | — |
| 2* | 2-3 mm | 8-12 mm | 12-17 mm | 7-10 mm | 1-2 mm |
| 3* | 3-4 mm | + | + | + | 1-2 mm |

—: No growth observed
+: Clear area spreading over the substantially entire area of the petri dish
*: The indicated size is a length of the clear area measured in one direction, since the colony was not substantially circular.

(2) Growth pH (at 30° C.)

1) LB (Luria Bertani) media (pH=7.8; 6.9; 5.9; 5.0; 4.0; 3.0; 1.9; and 1.0)

The growth condition of the bacteria on each medium is indicated in the following table, in terms of the optically measured density OD$_{660}$. After the 24 hours of incubation, the growth was saturated.

| LB Media pH | Time of Incubation | | | | | |
|---|---|---|---|---|---|---|
| | 4 hr. | 6 hr. | 8 hr. | 24 hr. | 4 days | 7 days |
| 7.8 | 0.87 | 1.15 | 1.27 | 1.33 | | |
| 6.9 | 0.70 | 1.23 | 1.32 | 1.41 | | |
| 5.9 | 0.56 | 1.28 | 1.39 | 1.53 | | |
| 5.0 | 0.003 | — | — | — | — | 0.003 |
| 4.0 | 0.007 | — | — | — | — | 0.008 |
| 3.0 | 0.010 | — | — | — | — | 0.005 |
| 1.9 | 0.015 | — | — | — | — | 0.018 |
| 1.0 | 0.019 | — | — | — | — | 0.023 |

It will be understood from the above table that the strain grew on the LB medium having pH values of 7.8, 6.9 and 5.9.

2) The culture liquid on each of the media having pH values of 5.0, 4.0, 3.0, 1.9 and 1.0 on which no bacteria growth appeared after seven days of incubation in the test above was transferred to a corresponding LB medium having a pH value of 7.0. A growth of the bacteria strain was found in each of the culture liquids obtained from the original LB medium of pH 5.0, 4.0 and 3.0. The test shows that the present strain of Achromobacter Bine-B grows well at pH values around neutraility, and is dormant under relatively highly acidic conditions.

| | |
|---|---|
| (3) Nitrate reduction | Negative |
| (4) H$_2$S production | Positive |
| (5) Indole formation | Negative |
| (6) V-P test | Negative |
| (7) O-F test | Negative |
| (8) Methyl red test | Positive |
| (9) Catalase | Positive |
| (10) Oxidase | Positive |
| (11) Urease | Negative |
| (12) Acid and gas production from carbohydrates | Neither acid nor gas produced from: Glucose; Saccharose; Rhamnose; Sorbitol; Xylose; Lactose; Galactose; Maltose; Mannose; Arabinose; Fructose; and Mannitol |
| (13) Anaerobic cultivation | Growth observed |

(IV) Identification a) Corynebacterium Bine-A

Judging from the above-described characteristics and properties of the present strain of bacteria, the strain appears to belong to a species of Corynebacterium, according to "Classification and Identification of Microorganisms", 2nd volume, Takeharu Hasegawa, Gakugei Publishing Company, Japan, and "Bergey's Manual of Systematic Biotechnology". However, the characteristics and properties of the present strain do not completely coincide with those of any known strain of Corynebacterium. Therefore, the present strain was named "Corynebacterium Bine-A".

b) Achromobacter Bine-B

The above-described characteristics and properties of the present strain indicate that the strain belongs to a species of Achromobacter, but do not completely coincide with those of any known strain of Achromobacter given in the above identified publications. Therefore, the present strain was named "Achromobacter Bine-B.

(V) Incubation of Strains

The strains of Corynebacterium Bine-A and Achromobacter Bine-B may be cultivated by an ordinary method used for cultivating Actinomycetes. For assuring chitinolytic activities of the bacteria, colloidal chitin or chitosan is used as a major carbon source of a culture medium, in combination with other suitable known carbon sources. As a nitrogen source of the medium, ammonium salt, nitrate, yeast extract and peptone may be used alone or in combination. As a phosphorus source, phosphate may be used. Other sources such as alkali metal salt, magnesium sulfate, iron sulfate, zinc sulfate and manganese chloride may be added as needed.

While a solid culture medium may be used, it is desirable to use a liquid culture medium generally used for producing enzymes. An example of a preferred liquid culture medium has a composition which consists of: 4 g of colloidal chitin; 0.7 g of K$_2$HPO$_4$; 0.3 g of KH$_2$PO$_4$; 0.5 g of MgSO$_4$. 5H$_2$O; 0.01 g of FeSO$_4$7-H$_2$O; 0.001 g of ZnSO$_4$; 0.001 g of MnCl; 0.25 g of yeast extract; 0.25 g of peptone; 15 g of agar; and 1000 ml of distilled water at pH7.0. The cultivation of the strain of Achromobacter Bine-B may be effected under either aerobic or anaerobic condition. For the strain of Corynebacterium Bine-A, the cultivation is effected by a shaking method under an aerobic condition, or a stirring and aeration method. Generally, the cultivation takes place at a temperature between 20° C. and 40° C.

According to one preferred form of the present invention, the strain of Corynebacterium Bine-A or Achromobacter Bine-B, or desirably a mixture containing both of these two strains is incubated or cultivated on a chitin or chitosan medium. Described specifically, the strain or strains is/are inoculated into a chitin or chitosan medium which contains a suitable amount of nutrient for microorganisms, and the medium is subjected to fermentation under an aerobic condition. This aerobic fermentation may be accomplished by leaving the medium in the atmosphere for a suitable number of days, with desired ancillary operations for aerobic fermentation, such as heating, stirring and forced aeration. The nutrient added to the chitin or chitosan medium may be rice bran, molasses or oil cake. The amount of addition of the nutrient is generally within a range of 0.05–20 parts by weight per one part by weight of chitin or chitosan. Then, a suitable volume of water is added to the culture medium consisting of chitin or chitosan and the nutrient, so that the content of the aqueous component of the medium is adjusted to a value (from 40% to 60%) that permits the fermentation.

The aerobically fermented material or product is then mixed with an additional amount of chitin or chitosan, and suitable amounts of calcium superphosphate, potassium chloride and nutrient (rice bran or molasses), so that the fermented material is aged. A medium for this aging generally consists of 0.1–1 part by weight of chitin or chitosan, 15–25 parts by weight of calcium superphosphate, 8–12 parts by weight of potassium chloride, 0.5–1.5 parts by weight of rice bran and 0.5–1.5 parts by weight of molasses, for one part by weight of the aerobically fermented material. The aging is effected for 10–40 days, with the aqueous content of the mixture held within a range of 40–60%, with heating and/or aeration of the mixture if and as needed. Thus, a solid culture material is prepared. This culture material may be used as an antibacterial composition, as described later.

In one embodiment of the present invention, a suitable volume of water is added to the thus obtained solid culture material, to prepare a mixture consisting of a liquid phase containing water-soluble component of the culture material, and a solid phase which consists of water-insoluble components of the culture material. Generally, the water volume to be added is equal to or up to about two-times the volume of the culture material. The mixture is then subjected to an ordinary solid-liquid separation process, to separate the liquid phase from the solid phase. Thus, the liquid phase is isolated as a culture liquid according to the invention. The obtained culture liquid contains not only pharmaceutically effective components produced during the incubation or cultivation of the strain or strains of bacteria, but also the cultures of the bacteria per se. Where chitosan is used as a culture medium, the eventually obtained culture liquid contains non-decomposed chitosan, low-molecular weight chitosan, chitosanase, oligosaccharide, and the cultivated strain or strains of chitinolytic bacteria (i.e., Corynebacterium Bine-A and/or Achromobacter Bine-B), which cooperate with each other to provide excellent antibacterial, anti-nematode and/or plant-cell activating activities. Where chitin is used as a culture medium, chitosan is produced as a result of decomposition of chitin, and the eventually obtained culture liquid contains pharmaceutically effective components similar to those indicated above.

The culture liquid obtained by the solid-liquid separation of the liquid phase from the above-indicated mixture (fermented material with added water) is a highly acidic liquid having a pH value of about 1–3, whereby the chitinolytic bacteria present in the culture liquid are kept dormant. For this reason, it is considered that the culture liquid may maintain its composition as produced, for a comparatively long storage period. Namely, the relatively high acidity of the culture liquid appears to contribute to the protection of the pharmaceutically effective components against decomposition, denaturation, digestion and putrefaction.

The chitinolytic bacteria or microorganisms (Corynebacterium Bine-A and/or Achromobacter Bine-B) present in the culture liquid prepared according to the present invention may be advantageously used to reproduce a similar culture liquid. For example, a cultivation cycle may be repeated by inoculating a portion of the culture liquid into a chitin or chitosan medium for aerobic fermentation and aging as described above, to reproduce a similar culture liquid.

The antibacterial, anti-nematode and/or plant-cell activating composition in the form of the culture liquid prepared according to the present invention may be applied to plants or soils, with or without dilution by a suitable diluent. Where the liquid is diluted for use, and the acidity of the diluted liquid increases to a pH value around neutrality, it appears that the bacteria present in the liquid start chitinolytic activities for producing physiologically active components. These physiologically active components to be produced by the bacteria are unstable in the presence of the bacteria, and are difficult to preserve for a long time, and are desirably applied to the plant cells or pathogenic bacteria or microbes as soon as they are produced. Where the non-diluted culture liquid is applied to seeds or diseased parts of plants, the acidity of the liquid does not permit pathogenic bacteria or insects to live or grow, thereby temporarily protecting the seeds or plants against the pathogenic bacteria or insects, while the bacteria (Corynebacterium Bine-A and/or Achromobacter Bine-B) present in the applied liquid are live under the relatively high acidic condition of the liquid. As the acidity of the applied liquid increases toward the neutrality due to natural dilution, the bacteria of the applied liquid becomes more and more active to produce physiologically active components, as described above.

Inventors' research and analysis up to the present do not reveal a sufficiently clear reason for the effect of the present culture liquid of resisting pathogenic bacteria and activating plant cells. However, it is presumed that the effect results from the following.

The components present in the culture liquid applied to a plant, such as chitosan, low-molecular weight chitosan and oligosaccharide of chitosan are absorbed by the plant. The absorbed components stimulate and activate the plant cells, promoting the transcription from DNA to RNA, and inducing biosynthesis of chitosan-decomposing enzyme (chitosanase) or chitin-decomposing enzyme (chitinase). Further, the components absorbed in the plant cells further function to promote the production of β-glucanase, and antibacterial or antimicrobial substance in the form of phenylammonia-lyase which is associated with the formation of phytoalexin or lignin. The activation of the plant cells increases the production of protein, carbohydrate and fat by the plant, and gives a resistance to diseases or maladies. The chitinase and chitonase present in the applied liquid and biosynthesized by the plant cells decompose chitin and chitosan of the cell walls of pathogenic bacteria, thereby destroying the bacteria walls. The antibacterial substances such as phytoalexin act on the destroyed bacteria walls, thereby inhibiting the growth of the pathogenic bacteria. The oligosaccharide of chitosan present in the culture liquid enters the cells of the pathogenic bacteria, thereby preventing the proliferation of the pathogenic bacteria. The chitosan and oligosaccharide of chitosan produced by decomposition of the cell walls of the pathogenic bacteria act on the cell walls of the plant so as to activate the plant cell walls. Further, the chitinolytic bacteria (Corynebacterium Bine-A and/or Achromobacter Bine-B) present in the rhizosphere of the plant function to cause chitinase and chitosanase to decompose the cell walls of the pathogenic bacteria, thereby protecting the rhizome of the plant from the pathogenic bacteria. In summary, it is presumed that the components of the culture liquid prepared according to the present invention directly or indirectly function to provide excellent antibacterial or anti-nematode, bacteriolysis activities for inhibiting the growth or proliferation of pathogenic bacteria. Moreover, the culture liquid facilitates the absorption of nutrients by plants, and stimulate or activate the plant cells, resulting in an increase in the production by the plants.

Thus, the culture liquid prepared according to the present invention may be effectively used as a pharmaceutic composition or agent for pathogenic bacteria and nematodes and/or as an activator for activating plant cells. In particular, the present culture liquid is effective for protecting plants against pathogenic bacteria containing chitin or chitosan. For instance, the present liquid exhibits particularly high antibacterial activities against: crown gall of roses and chrysanthemum; damping-off and fairy ring spot of carnation; soft rot of orchid and cabbage; fusarium wilt or gummy stem blight, and microbial dwarf of melon; and diseases of rice plants, flowers and green vegetables during growth of seedlings, cuttings or saplings. The liquid exhibits excellent anti-nematode or insecticidal activities, particularly, to nematodes of pine trees and root-knot nematodes of tomato.

The plant-cell activating activities of the present culture liquid provide particularly excellent results such as: growth of sound seedlings of carnation (by applying the present liquid to both the parent and the seedlings), the carnation seedlings being generally easily susceptible to damage during the transplantation; increased crop of peas, the application of the liquid allowing the transplantation of the seedlings; increased crop of common or French beans; increased crop of soybeans, the use of the liquid enabling machine harvesting of the soybeans; improved quality and increased crop of chrysanthemum coronarium; increased saccharide concentration of melon; improved quality and increased crop of cucumber; and increased crop of rice, the use of the liquid increasing the standing strength of the rice plants.

The present culture liquid may be applied to subject plants in suitable manners as used for the known agricultural chemicals. For example, the liquid is sprayed or coated directly over the diseased parts of the plants, or applied to the seeds of the plants before planting or bedding. Alternatively, the diluted liquid is sprayed over the plants, or the seedlings, saplings or cuttings of the plants are immersed in the diluted liquid before planting.

In a second embodiment of the present invention, the solid culture material obtained by the incubation of the strain of Corynebacterium Bine-A and/or strain of Achromobacter Bine-B on chitin or chitosan culture medium followed by the fermentation and aging of the culture medium is used as a solid antibacterial or antimicrobial agent or composition. In one form of this embodiment, a suitable phosphorus source substance such as rice bran, and a suitable nitrogen source substance such as oil cake are evenly mixed with the prepared solid culture material, and the mixture is left under aeration in the atmosphere for 15–30 days, for natural aging of the material. The thus treated solid culture material is also effectively used as an antibacterial agent.

While an organic material such as oil cake may be used as the nitrogen source, a 50–70% fermented legume forage is a particularly preferred nitrogen source. For 100 parts by weight of the solid culture material, the aging nutrient generally consists of 6–12 parts by weight of the phosphorus source substance, and 200–600 parts, preferably about 400 parts by weight of the nitrogen source substance.

In the first embodiment, the liquid phase of the mixture obtained by adding water to the solid culture material is separated as the culture liquid, by a suitable solid-liquid separation method. However, the solid phase rather than the liquid phase may also be used for preparing a solid antibacterial composition. In this third embodiment of the invention, suitable phosphorus and nitrogen source substances are added to the separated solid phase, and chitosan is evenly mixed with the mixture. The final mixture is aged in the same manner as described above with respect to the preferred form of the preceding second embodiment of the invention.

In the above embodiment, 3–6 parts by weight of the phosphorus source substance, 100–300 parts (preferably about 200 parts) by weight of the nitrogen source substance, and 2–3 parts of chitosan are added to 100 parts by weight of the separated solid phase.

The solid antibacterial compositions according to the second and third embodiments of the invention exhibit excellent antibacterial or antimicrobial activities, and are particularly suitable for curing or preventing diseases or maladies of plants which are caused by bacteria or microbes containing chitin or chitosan. For example, the compositions are effective to white root rot of peach, apple, pear, grape and loquat. Since the compositions are solid, the pharmaceutical effect of the compositions is slow and continues for a comparatively long time.

The solid antibacterial compositions may be applied in the same manner as used for known solid pharmaceutics or chemicals. For example, the compositions are applied directly to diseased parts of plants, or to the rhizosphere of the soil. In the latter case, a suitable amount of the antibacterial composition is put in several holes having depths determined so that the composition in each hole is a suitable distance above the diseased parts of the plant root. The holes are re-filled with the soil.

To clarify the concept of the present invention, some examples of the present invention will be given below.

However, it is to be understood that the invention is not limited to the details of the illustrated examples, and that the invention may be embodied with various changes, modifications and improvements, which may occur to those skilled in the art, without departing from the spirit and scope of the invention.

Preparation of Culture Liquid (Pharmaceutic Composition)

Initially, a culture medium consisting of 1 kg of powdered chitosan, 0.2 kg of rice bran, 0.2 kg of molasses and 0.6 kg of oil cake was prepared. A liquid containing culture of the above-identified strains of Corynebacterium Bine-A and Achromobacter Bine-B was inoculated into the prepared culture medium. The thus obtained mixture was adjusted so that the content of the aqueous component was about 50%. The mixture was aerobically fermented while being left in the atmosphere for ten days.

To the aerobically fermented mixture, there were added 20 parts by weight of calcium superphosphate, 10 parts by weight of potassium chloride, 1 part by weight of rice bran, 1 part by weight of molasses and 0.5 part by weight of chitosan, for 1 part by weight of the fermented mixture. The thus prepared mixture was aged at the room temperature for one month.

A volume of water equal to the volume of the prepared culture material was added, and the liquid phase containing water-soluble components of the culture material was separated from the solid phase consisting of the water-insoluble components of the culture material. Thus, the final culture liquid was prepared. This culture liquid has a relatively high degree of acidity, and contains about $2.2 \times 10^5$, chitinolytic bacteria (i.e., Corynebacterium Bine-A and Achromobacter Bine-B) per 1 ml of the liquid, which grow on the chitin medium.

Remedy Test of Culture Liquid Applied to Cure Crown Gall of Roses (1) First Test To check the present culture liquid for its effect of curing crown gall of roses, the diseased parts of the roots of the specimen roses (varieties: "Sonia" and "Izumo") were initially treated by removing the outer skin, and a 5 ml volume of the culture liquid was sprayed over the diseased parts of each specimen. On the fifth day after the application of the culture liquid, it was confirmed that the crown gall of each of the two varieties of the specimen roses was considerably diminished. On the fifteenth day, the crown gall of the specimen rose "Izumo" was completely cured. On the twentieth day, the crown gall of the other specimen rose "Sonia" was completely cured. Thus, the test revealed an excellent effect with respect to the crown gall of roses.

(2) Second Test

The following test was conducted to determine a remedial effect of the present culture liquid with respect to stocks of roses which suffer from crown gall. As the specimen roses, four varieties "Rosa multi flora", "Rosa multc flora K-1", "Rosa multc flora K-2" and "Tsukushino Ibara" were used. For each variety, ten to thirteen cuttings were initially planted in "Pearlite" soils in plastic pots. The soils were impregnated with a liquid obtained by grinding or mashing crown galls of roses. One month after the planting of the cuttings, each cutting was transplanted in a steam-sterilized soil in a plastic pot. Upon the transplantation, and seven days after the transplantation, a 300 ml volume of the 100-fold diluted culture liquid was applied to the soil in each plastic pot. Six months after the transplantation of the cuttings, the stocks which have grown up from the cuttings were removed from the pots, and were checked for the presence of the crown gall.

The test results are indicated in the following tables, in which Specimen Nos. 3, 6, 9 and 12 represent the stocks of the four varieties "Rosa multc flora", "Rosa multc flora K-1", "Rosa multc flora K-2" and "Tsukushino Ibara", respectively, which were tested in the manner as described above. Specimen Nos. 1, 4, 7 and 10 represent comparative stocks which were neither initially exposed to the liquid of the crown gall, and nor treated with the present culture liquid. Specimen Nos. 2, 5, 8 and 11 represent comparative stocks which were initially exposed to the liquid of the crown gall, but were not treated with the culture liquid.

| Variety | Specimen No. | Crown Gall Exposure | Application of Culture Liquid | Number of Stocks |
|---|---|---|---|---|
| Rosa multc flora | 1 | No | No | 12 |
| | 2 | Yes | No | 13 |
| | 3 | Yes | Yes | 10 |
| Rosa multc flora K-1 | 4 | No | No | 10 |
| | 5 | Yes | No | 13 |
| | 6 | Yes | Yes | 10 |
| Rosa multc flora K-2 | 7 | No | No | 10 |
| | 8 | Yes | No | 10 |
| | 9 | Yes | Yes | 10 |
| Tsukushino Ibara | 10 | No | No | 10 |
| | 11 | Yes | No | 12 |
| | 12 | Yes | Yes | 11 |

| Specimen No. | Number of Stocks Attacked by Crown Galls | Attack Ratio | Number of Crown Galls Having Different Sizes | | |
|---|---|---|---|---|---|
| | | | 2–10 mm | 10–20 mm | 20 mm ~ |
| 1 | 2 | 16.7% | 2 | 0 | 0 |
| 2 | 6 | 46.2% | 2 | 1 | 3 |
| 3 | 1 | 10.0% | 1 | 0 | 0 |
| 4 | 1 | 10.0% | 1 | 0 | 0 |
| 5 | 4 | 30.8% | 1 | 2 | 1 |
| 6 | 1 | 10.0% | 1 | 0 | 0 |
| 7 | 0 | 0% | 0 | 0 | 0 |
| 8 | 3 | 30.0% | 2 | 0 | 1 |
| 9 | 1 | 10.0% | 1 | 0 | 0 |
| 10 | 2 | 20.2% | 2 | 0 | 0 |
| 11 | 8 | 66.7% | 7 | 1 | 0 |
| 12 | 3 | 27.3% | 3 | 0 | 0 |

| Specimen No. | Total Crown Gall Weight | Total Weight of All Stocks | Total Root Weight of All Stocks |
|---|---|---|---|
| 1 | 0.2 g | 65.6 g | 21.0 g |
| 2 | 27.0 g | 99.3 g | 48.8 g |
| 3 | 0.3 g | 216.2 g | 75.0 g |
| 4 | 0.1 g | 32.9 g | 11.7 g |
| 5 | 8.7 g | 64.9 g | 26.3 g |
| 6 | 0.1 g | 64.3 g | 21.0 g |
| 7 | 0 g | 56.0 g | 22.3 g |
| 8 | 3.1 g | 45.9 g | 18.7 g |
| 9 | 0.4 g | 66.0 g | 25.3 g |
| 10 | 0.7 g | 52.8 g | 20.3 g |
| 11 | 3.5 g | 119.2 g | 44.5 g |
| 12 | 1.3 g | 96.4 g | 34.9 g |

It will be understood from the above tables that the culture liquid prepared according to the present invention is effective to protect the stocks of roses against attack by the crown gall, without adversely influencing the growth of the stocks.

Application of Culture Liquid to Garden Peas Upon Transplantation

Seeds of garden peas (variety: "Snack") were planted in late November in a bed of river sand. The seeds were germinated, and the seedlings were transplanted in the middle of December. Five days before the transplanation, a 2 volume of the 100-fold diluted culture liquid prepared as described above was applied to the seedlings, per square meter of the seedbed.

The transplanted seedlings (to which the culture liquid was applied) grew without damage due to the transplantation, faster than comparative specimens of the same variety whose seeds were planted directly in field and which grew comparatively slowly from early December. The growth (height and number of branches) of the transplanted seedlings exceeded that of comparative podded peas which were seeded in early November. The transplanted plants bloomed in early March in the next year, ten days earlier than the directly seeded specimen, and had more pods than the directly planted specimens at the time of blooming. In the middle of June, a typical one of the directly seeded specimens had a total of eight vines (four primary vines growing from the seed, and four branches extending from lower portions of the vines just above the soil surface). The vines have 10, 11 or 12 arrays of pods. The three vines had 12 arrays of pods. On the other hand, a typical one of the transplanted plants whose seedlings were treated by the culture liquid had a total of 22 vines (including 13 branches). The vines had 13 or 14 arrays of pods. The ten vines had 14 arrays of pods.

The test shows that the application of the present culture liquid permits fast and sound growth of transplanted garden peas, and increased crop of the peas, although the transplantation of the seedlings of peas generally results in poor growth and reduced crop.

Remedy Test of Culture Liquid Applied to Cure Root-Knot Nematodes of Tomato

Seeds of tomato (variety: "Momotaro") were planted in a bed impregnated with the 50-fold diluted culture liquid. Upon transplantation of the seedlings which have grown up on the bed, the seedlings were immersed in the 100-fold diluted culture liquid. Comparative seedlings were grown and planted without the use of the culture liquid.

An examination of the rhizomes of the tomato plants showed the absence of any root knots on the plants whose seedlings were treated with the culture liquid, and the presence of several root knots on each plant of the non-treated specimens.

Test of Culture Liquid As Insecticide for Pine Tree Nematodes

The culture liquid was applied to pine tree nematodes known as a pine weevil, which is considered a major cause for early dying of pine trees. Graph of the accompanying drawing indicates the result of the test at 4° C. and 25° C., by using the 4-fold diluted liquid and the 2-fold diluted liquid. It will be understood from the graph that the culture liquid effectively functions as an insecticide, under the 4° C. and 25° C. test conditions. In particular, more than 90% of the specimens were dead at 25° C. 24 hours after the application of the culture liquid.

As described above, the strain of Corynebacterium named "Corynebacterium Bine-A", the strain of Achromobacter named "Achromobacter Bine-B", or a combination of these two strains provides a culture liquid which decomposes chitin or chitosan and exhibits excellent antibacterial, anti-nematode and plant-cell activating activities. The present culture liquid is effective to cure or prevent: crown gall of roses and chrysanthemum; fusarium wilt or gummy stem blight, and microbial dwarf of melon; soft rot of orchid (variety: Phalaenopsis Aphrodite) and cabbage; and damping-off and fairy ring spot of carnation. The culture liquid is an effective insecticide for pine tree nematodes and root knot nematodes of tomato, and is effective to prevent diseases of flowers and green vegetables during growth of seedlings, cuttings or saplings. The liquid also exhibits excellent plant-cell activating activities, preventing damage of seedlings or saplings upon planting, permitting the transplantation of seedlings of peas, increasing the standing strength of rice plants, and assuring improved quality and increased amount of crops.

Preparation of Solid Composition (Pharmaceutic Composition) from Culture Material Initially, a culture medium consisting of 1 kg of powdered chitosan, 0.2 kg of rice bran, 0.2 kg of molasses and 0.6 kg of oil cake was prepared. A liquid containing culture of strains of Corynebacterium Bine-A and Achromobacter Bine-B was inoculated into the prepared culture medium. The thus obtained mixture was adjusted so that the content of the aqueous component was about 50%. The mixture was aerobically fermented while being left in the atmosphere for ten days.

To the aerobically fermented mixture, there were added 20 parts by weight of calcium superphosphate, 10 parts by weight of potassium chloride, 1 part by weight of rice bran, 1 part by weight of molasses and 0.5 part by weight of chitosan, for 1 part by weight of the fermented mixture. The thus prepared mixture was aged at the room temperature for one month. Thus, a solid culture material was prepared.

To the prepared solid culture material, there was added the same volume of water. The solid phase was separated by an ordinary solid-liquid separation method. Then, 5 parts by weight of rice bran, 200 parts by weight of oil cake and 3 parts by weight of chitosan were evenly mixed with 100 parts by weight of the separated solid composition. The obtained mixture was left under aeration in the atmosphere for 30 days, for natural aging of the composition. In this manner, a solid antibacterial pharmaceutic composition was prepared.

Remedy Test of Antibacterial Composition Applied to Cure White Root Rot of Pear Tree To check the prepared solid antibacterial composition for its effect of curing white root rot of peach trees, six holes having depths of 20-30cm were dug in the rhizosphere of each of twenty diseased pear trees (variety: "Kosui"), such that the depth of each hole was above the diseased parts of the rhizome of the tree. Four of the twenty specimen trees were about to die due to white root rot. A 0.7 kg mass of the solid composition was introduced into each hole, and the hole was refilled with the soil.

All of the thus treated specimens gradually recovered from the disease, with the initially yellow leaves changing to green leaves, while the branches and the buds grew healthily. Three months after the present antibacterial composition was applied to the specimen trees, all the trees were completely recovered. While the saccharide concentration of the pears during the period of disease was 8 degrees or lower, the saccharide concentration after the recovery increased to 12 degrees or higher, and the pears were qualified to be delivered or marketed.

As described above, the solid antibacterial composition prepared from the culture material obtained by incubating at least one of the strains of Corynebacterium Bine-A and Achromobacter Bine-B exhibits excellent antibacterial activities against various bacteria such as Rosellinia necatrix Prillieux which cause white root rot of pear trees and other trees. While the effect of this solid composition does not appear immediately after the application, the effect continues for a relatively long time because the composition remains in the solid phase at the point of application.

What is claimed is:

1. A composition consisting of a highly acidic culture liquid obtained by a process comprising the steps of:
    preparing a culture material by incubating on a culture medium containing chitin or chitosan, a strain selected from the group consisting of Corynebacterium Bine-A, having an accession number FERM BP-2879, Achromobacter Bine-B, having an accession number FERM BP-2880, and a combination thereof;
    adding water to said culture material, to obtain a mixture consisting of a liquid phase containing water-soluble components of said culture material and a solid phase consisting of waterinsoluble components of said culture material; and
    separating said liquid phase as said culture liquid from said solid phase.

2. An antibacterial composition consisting of a solid culture material prepared by (a) incubating on a culture medium containing chitin or chitonan, a strain selected from the group consisting of Corynebacterium Bine-A, having an accession number FERM BP-2879, Achromobacter Bine-B, having an accession number FERM BP-2880, and a combustion thereof and (b) recovering the solid culture material.

3. A solid antibacterial composition prepared by a process comprising the steps of:
    preparing a solid culture material by incubating on a culture medium containing chitin or chitosan, a strain selected from the group consisting of Corynebacterium Bine-A, having an accession number FERM BP-2879, Achromobacter Bine-B, having an accession number FERM BP-2880, and a combination thereof;
    mixing a phosphorus source and a nitrogen source with said solid culture material;
    aging a mixture of said solid culture material and said phosphorus and nitrogen sources; and
    recovering the solid culture material.

4. A solid antibacterial composition prepared by a process comprising the steps of:
    preparing a solid culture material by incubating on a culture medium containing chitin or chitosan, a strain selected from the group consisting of Corynebacterium Bine-A, having an accession number FERM BP-2879, Achromobacter Bine-B, having an accession number FERM BP-2280,and a combination thereof;
    adding water to said solid culture material to prepare a water- containing culture having a liquid phase and a solid phase;
    separating said solid phase of said water-containing culture from said liquid phase by solid-liquid separation;
    mixing a phosphorus source, a nitrogen source and chitosan with said solid phase; and
    aging a mixture of said solid phase, said phosphorus and nitrogen sources and said chitosan.

* * * * *